United States Patent
Shriver et al.

(10) Patent No.: US 8,921,116 B2
(45) Date of Patent: *Dec. 30, 2014

(54) METHODS OF EVALUATING DIETHYLAMIDE IN PEPTIDE MIXTURES FOR THE PREPARATION OF GLATIRAMER ACETATE

(71) Applicant: Momenta Pharmaceuticals, Inc., Cambridge, MA (US)

(72) Inventors: Zachary Shriver, Cambridge, MA (US); Ganesh V. Kaundinya, Bedford, MA (US); Jonathan C. Lansing, Reading, MA (US); Corinne Bauer, Sudbury, MA (US); Xiangping Zhu, North Grafton, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,650

(22) Filed: Jun. 24, 2013

(65) Prior Publication Data

US 2014/0011727 A1    Jan. 9, 2014

Related U.S. Application Data

(63) Continuation of application No. 12/298,591, filed as application No. PCT/US2007/067777 on Apr. 30, 2007, now Pat. No. 8,470,603.

(60) Provisional application No. 60/746,018, filed on Apr. 28, 2006.

(51) Int. Cl.
  *A61K 38/02*    (2006.01)
  *G01N 24/08*    (2006.01)
  *G01N 1/28*    (2006.01)
  *G01N 33/94*    (2006.01)
  *G01N 33/15*    (2006.01)
  *G01N 33/68*    (2006.01)

(52) U.S. Cl.
  CPC ............ *G01N 33/9493* (2013.01); *G01N 33/15* (2013.01); *G01N 33/68* (2013.01); *G01N 33/6848* (2013.01); *G01N 33/6806* (2013.01); *G01N 33/6821* (2013.01); *A61K 38/02* (2013.01)
  USPC .............. 436/86; 436/173; 436/175; 514/1.1; 530/300; 530/350

(58) Field of Classification Search
  None
  See application file for complete search history.

(56) References Cited

U.S. PATENT DOCUMENTS

| | | |
|---|---|---|
| 5,800,808 A | 9/1998 | Konfino et al. |
| 6,514,938 B1 | 2/2003 | Gad et al. |
| 8,470,603 B2 | 6/2013 | Shriver et al. |
| 2003/0134829 A1 | 7/2003 | Reed et al. |
| 2003/0153007 A1 | 8/2003 | Chen et al. |
| 2007/0054857 A1 | 3/2007 | Pinchasi et al. |

FOREIGN PATENT DOCUMENTS

| | | |
|---|---|---|
| JP | 2003-517002 | 5/2003 |
| WO | WO 2001/44268 | 6/2001 |
| WO | WO 2005/085323 | 9/2005 |
| WO | WO 2006/028958 | 3/2006 |
| WO | WO 2006/029411 | 3/2006 |

OTHER PUBLICATIONS

Bichsel et al., "Requirements for the quality control of chemically synthesized pepides and biochemically produced proteins," Pharmaceutica Acta Helvetiae 71 (1996) 439-446.
Ivanov et al., "Conformational States of Methylamides of N-Acetyl apha-Amino Acids and their N-Methyl Derivatives. II. 1H NMR Spectra," Khimiya Prirodnykh Soedinenii 1973, 339-348; translated in Chemistry of Natural Compounds, 9, 320-327.
Predicted 1 H NMR shifts of Alanine-Alanine dipeptide with C-terminal diethylamide. Generated with ChemDraw Ultra version 12.0 (2009) CambridgeSoft.
Rutherford, "NMR Spectroscopic Studies of Lithium Diethylamide: Insights into Ring Laddering", J. of American Chem Soc., 121(43):10198-10202, 1999.
Tarcic et al., "Copolymer 1 (Copaxone) from an idea to a drug for treatment of multiple sclerosis," Kimiya, Handasa Kimit, vol. 28, pp. 14, 16-18 (1997); Scifinder English Abstract.
Yang et al., "Drug acyl glucuronides: Reactivity and analytical implication" Curr. Pharmac. Analysis (Netherlands) vol. 2(3):259-277, 2006.

*Primary Examiner* — Yelena G Gakh
*Assistant Examiner* — Michelle Adams
(74) *Attorney, Agent, or Firm* — Fish & Richardson P.C.

(57) ABSTRACT

The presently disclosed subject matter provides methods for evaluating and characterizing peptides, peptide mixtures, and polypeptide mixtures. More particularly, the presently disclosed subject matter provides methods for evaluating or characterizing complex peptide or polypeptide mixtures comprising glutamic acid, alanine, tyrosine, and lysine, e.g., Copolymer-1 or glatiramer acetate, including, but not limited to, methods of identifying, isolating, quantifying, and purifying amino acids, peptides, polypeptides, and combinations thereof having a diethylamide group instead of a carboxyl group present on the C-terminus. The presently disclosed methods can be used to determine the mole percent of polypeptides having a diethylamide group at a C-terminus thereof and can be used to evaluate one or more properties of a sample of one polypeptide mixture as compared to one or more properties of a different sample of a polypeptide mixture.

7 Claims, 9 Drawing Sheets

METHODS OF EVALUATING DIETHYLAMIDE IN PEPTIDE MIXTURES FOR THE PREPARATION OF GLATIRAMER ACETATE

TECHNICAL FIELD

The presently disclosed subject matter generally relates to methods of characterizing peptides, peptide mixtures, and polypeptide mixtures. More particularly, the presently disclosed subject matter relates to methods of characterizing complex peptide or polypeptide mixtures comprising glutamic acid, alanine, tyrosine, and lysine, including, but not limited to, methods of identifying, isolating, quantifying, and purifying amino acids, peptides, polypeptides, and combinations thereof, having a diethylamide group instead of a carboxyl group present on at least one end thereof.

BACKGROUND

Copolymer-1 is a complex mixture of polypeptides prepared from the polymerization of the amino acids glutamic acid, lysine, alanine and tyrosine. Copolymer-1 also is known as glatiramer acetate (CAS No. 147245-92-9) and has the following structural formula:

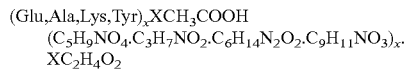

See *Physician's Desk Reference*, Thomson PDR, Montvale, N.J., p. 3297 (2007).

Glatiramer acetate (GA) is the active ingredient of COPAXONE® (Teva Pharmaceutical Industries Ltd., Israel), which comprises the acetate salts of synthetic polypeptides containing four naturally occurring amino acids: L-glutamic acid, L-alanine, L-tyrosine, and L-lysine, with a reported average molar fraction of 0.141, 0.427, 0.095, and 0.338, respectively. Id. Glatiramer acetate has been widely used in the treatment of multiple sclerosis and has been clinically shown to reduce the average relapse rate in people with the relapsing-remitting form of multiple sclerosis (RRMS).

Analytical tests that can be used to characterize glatiramer acetate are of benefit toward defining the structure of this complex peptide mixture and similar complex peptide mixtures. Such analytical methods also are useful for analyzing the properties or quality of a particular batch of the mixture, for analyzing intermediate stages in the preparation of glatiramer acetate, or for identifying and isolating bioreactive components of a complex mixture or signature components of the process for making the same. Thus, there is a need in the art for analytical tests that can be used to characterize glatiramer acetate and similar complex peptide mixtures. The presently disclosed subject matter addresses, in whole or in part, these and other needs in the art.

BRIEF SUMMARY

In some embodiments, the presently disclosed subject matter provides a method for detecting a modification of at least one C-terminus of one or more amino acids, peptides, polypeptide chains, and combinations thereof in a sample, the method comprising: (a) providing a sample suspected of containing one or more amino acids, peptides, polypeptide chains, and combinations thereof having at least one modified C-terminus; and (b) analyzing the sample by a method capable of detecting a modification of at least one C-terminus of an amino acid, peptide, polypeptide chains, and combinations thereof in the sample. The sample can be a polypeptide mixture including, but not limited to, Copolymer-1 or polymeric precursors thereof (e.g., the intermediates I, II and III shown in FIG. 1), derivatized Copolymer-1 or polymeric precursors thereof, fragmented Copolymer-1 or polymeric precursors thereof, fractionated Copolymer-1 or polymeric precursors thereof, and combinations thereof.

The modification of at least one C-terminus can include at least one C-terminus of the one or more amino acids, peptides, polypeptide chains, and combinations thereof in the sample having a diethylamide moiety bound thereto. The method capable of detecting a modification of at least one C-terminus of one or more polypeptide chains in the sample includes, but is not limited to, liquid chromatography, ion chromatography, gas chromatography, capillary electrophoresis, mass spectrometry, liquid chromatography/mass spectrometry, NMR spectroscopy, an antibody detection method, Raman spectroscopy, infrared spectroscopy, fluorescence spectroscopy, UV-Vis spectroscopy, gel electrophoresis, and combinations thereof. The presently disclosed methods also can include depolymerizing or fragmenting the sample, fractionating the sample, and purifying the sample.

In some embodiments, the presently disclosed subject matter provides a method for evaluating a sample comprising a polypeptide mixture, the method comprising: (a) providing a sample comprising a mixture of polypeptides, wherein one or more of the polypeptides are suspected of having a diethylamide moiety bound to a C-terminus thereof; (b) depolymerizing the sample to liberate diethylamine from one or more polypeptides having a diethylamide moiety bound to a C-terminus thereof, when one or more polypeptides having a diethylamide moiety bound to a C-terminus are present in the sample; and (c) analyzing the depolymerized sample to determine the presence or amount of liberated diethylamine therein.

The diethylamine can be detected by a method including, but not limited to, gas chromatography (GC), GC-MS, HPLC, LC-MS, NMR, antibody detection methods, Raman spectroscopy, capillary electrophoresis, liquid chromatography, gas chromatography, and ion chromatography, or in some embodiments, the method further comprises derivatizing the liberated diethylamine with a chromophore to form derivatized diethylamine and detecting the derivatized diethylamine by HPLC.

In some embodiments, the presently disclosed subject matter provides a method of assaying a sample of Copolymer-1, the method comprising: (a) providing a sample of Copolymer-1, wherein the sample of Copolymer-1 is suspected of comprising one or more polypeptides having a diethylamide moiety bound to a C-terminus thereof; (b) determining the presence or amount of polypeptides having a diethylamide moiety bound to a C-terminus thereof in the Copolymer-1 sample.

In some embodiments, the method further comprises comparing the amount of polypeptides having a diethylamide moiety bound to a C-terminus thereof in the Copolymer-1 sample to a predetermined reference value, wherein the reference value includes, but is not limited to, a specification value, a control value, and a value obtained from a direct measurement of a reference sample of Copolymer-1, such as glatiramer acetate, or a polymeric precursor thereof (e.g., one of the intermediates I, II and III shown in FIG. 1).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
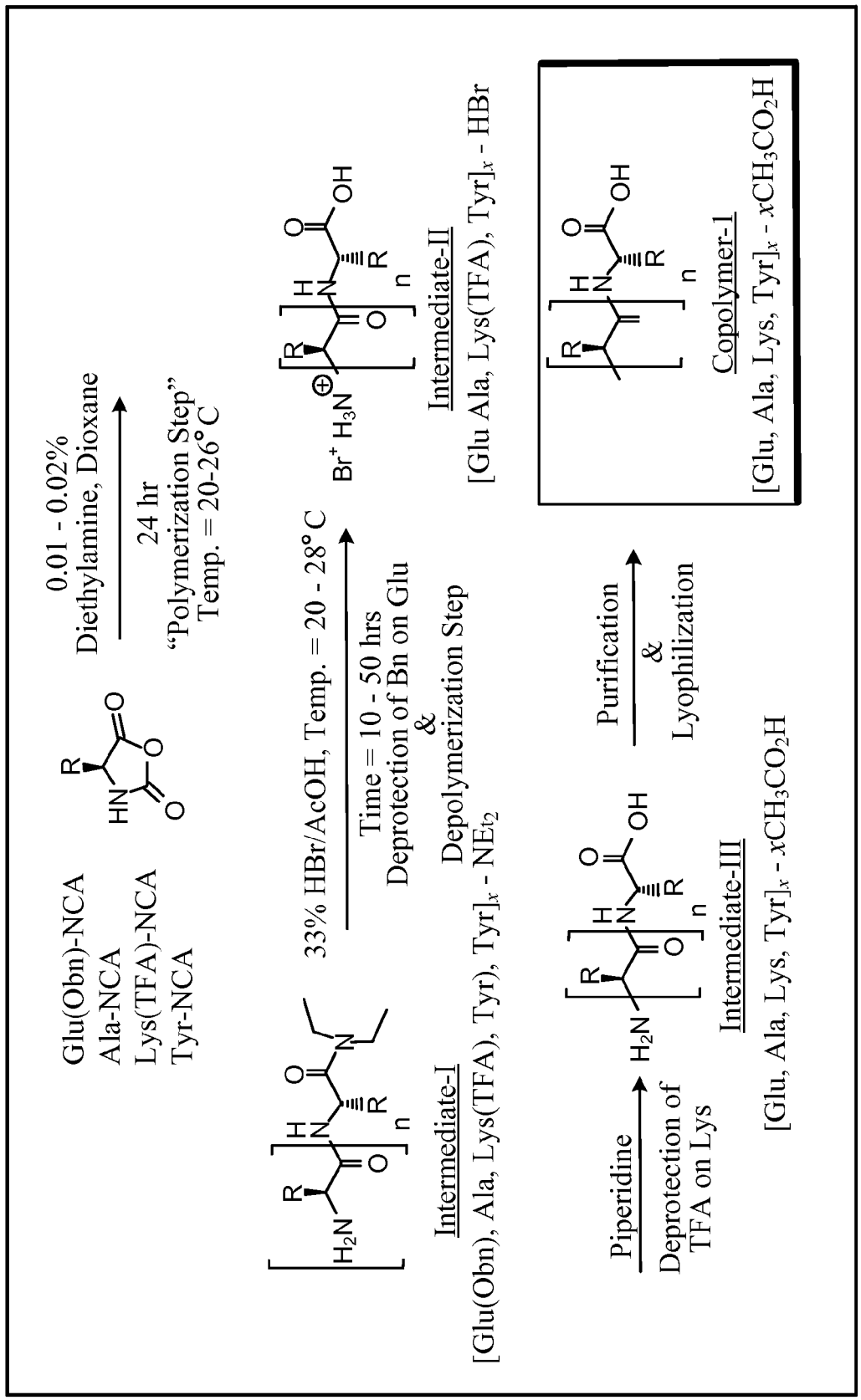
Figure 2:
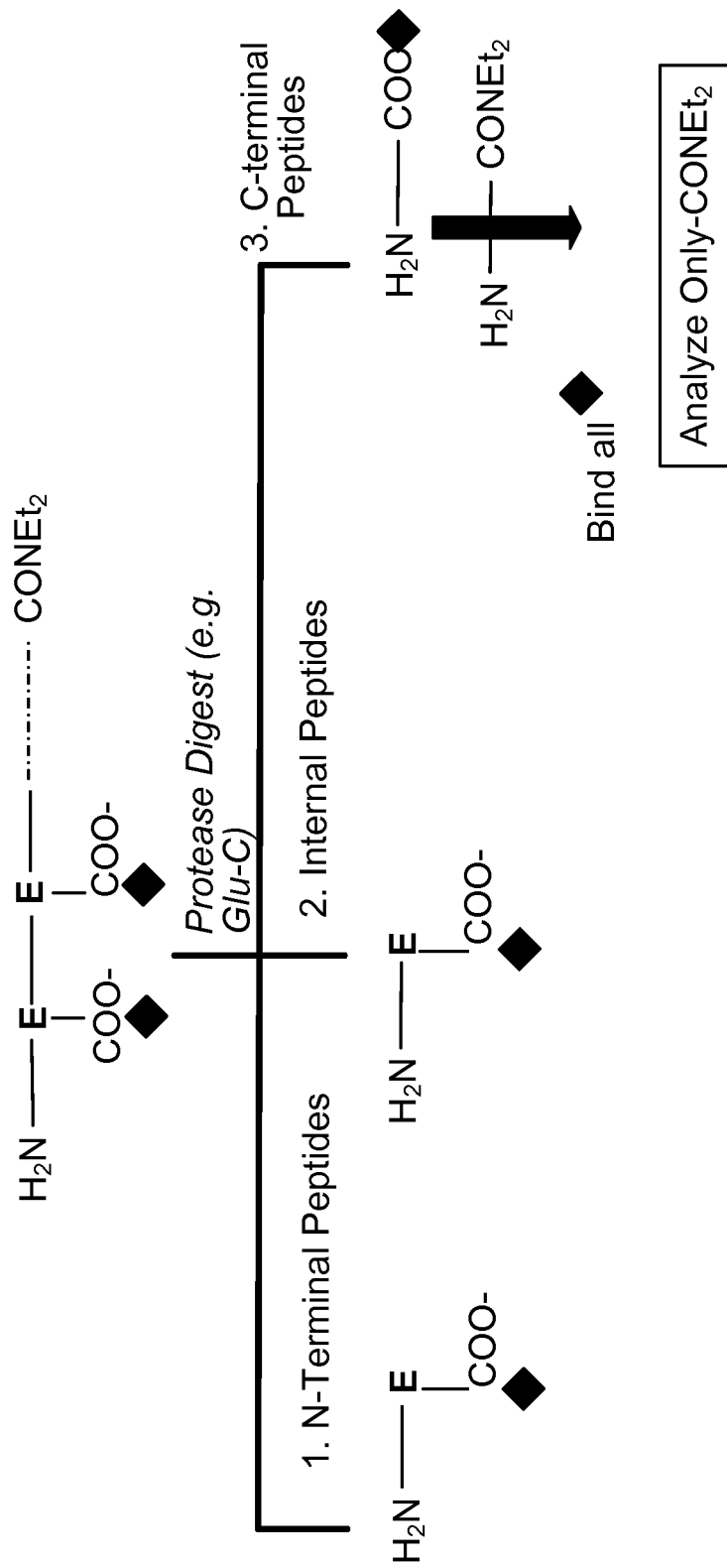
Figure 3:
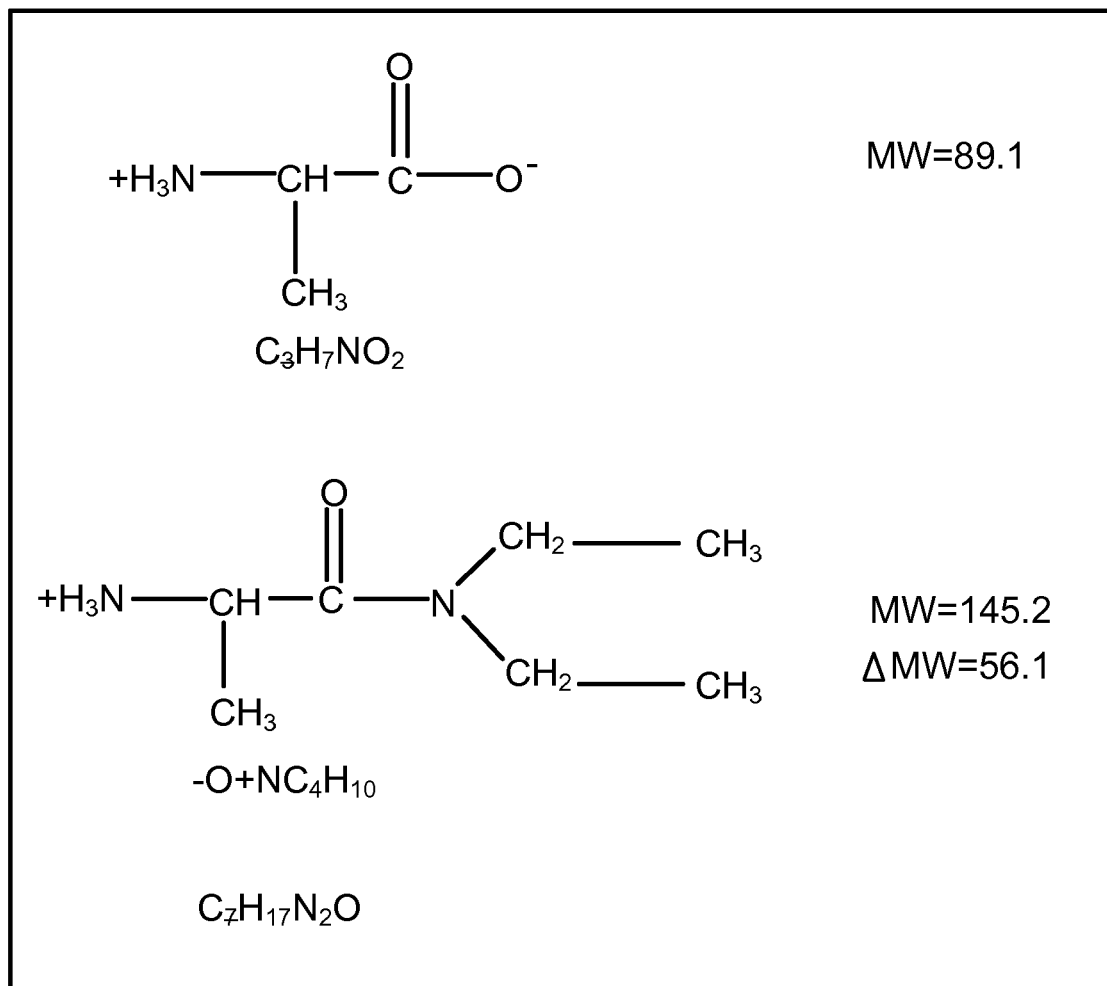
Figure 4:
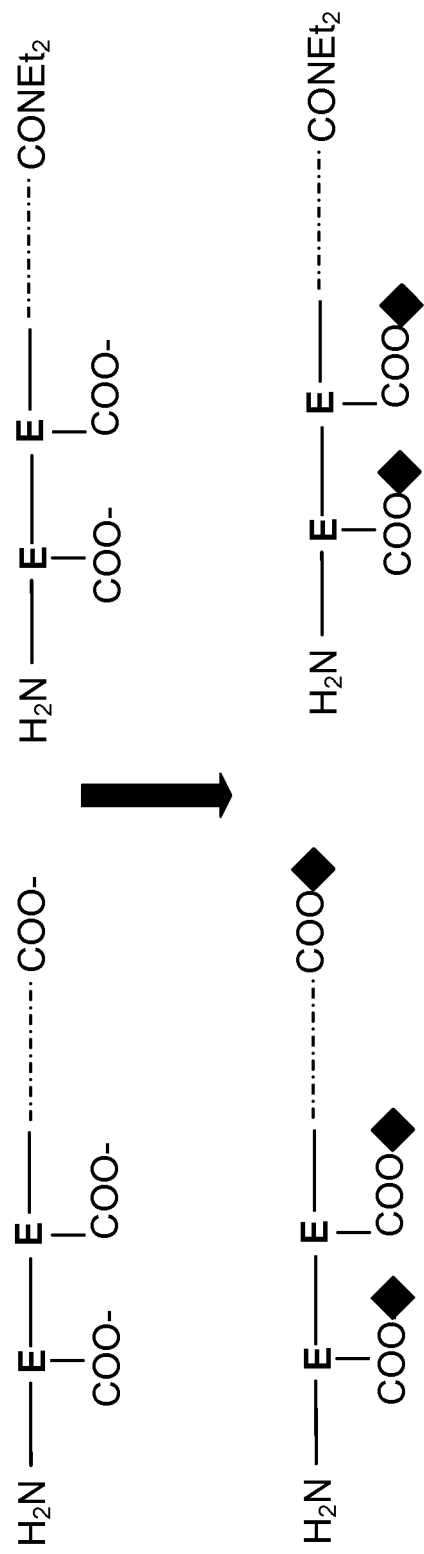
Figure 5:
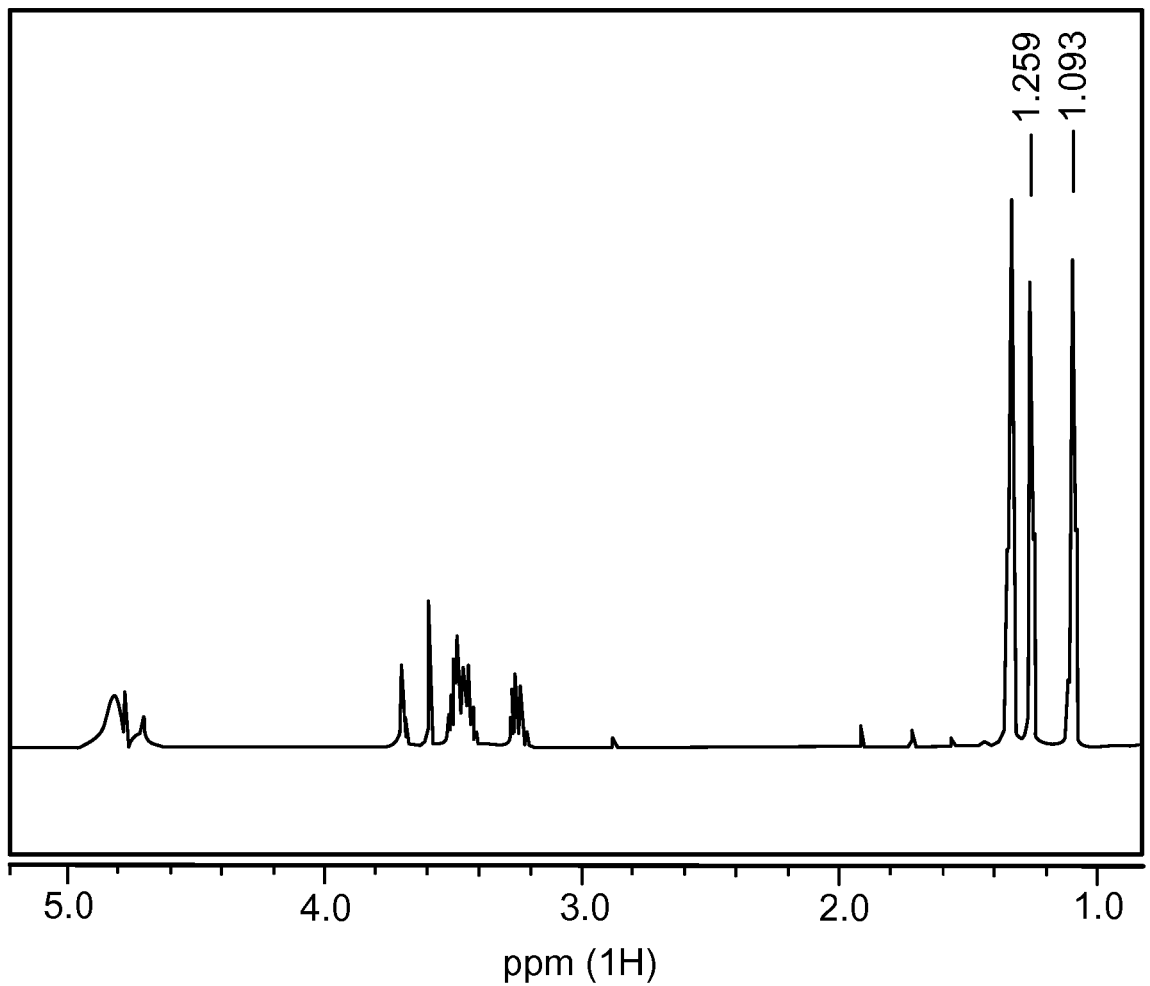
Figure 6:
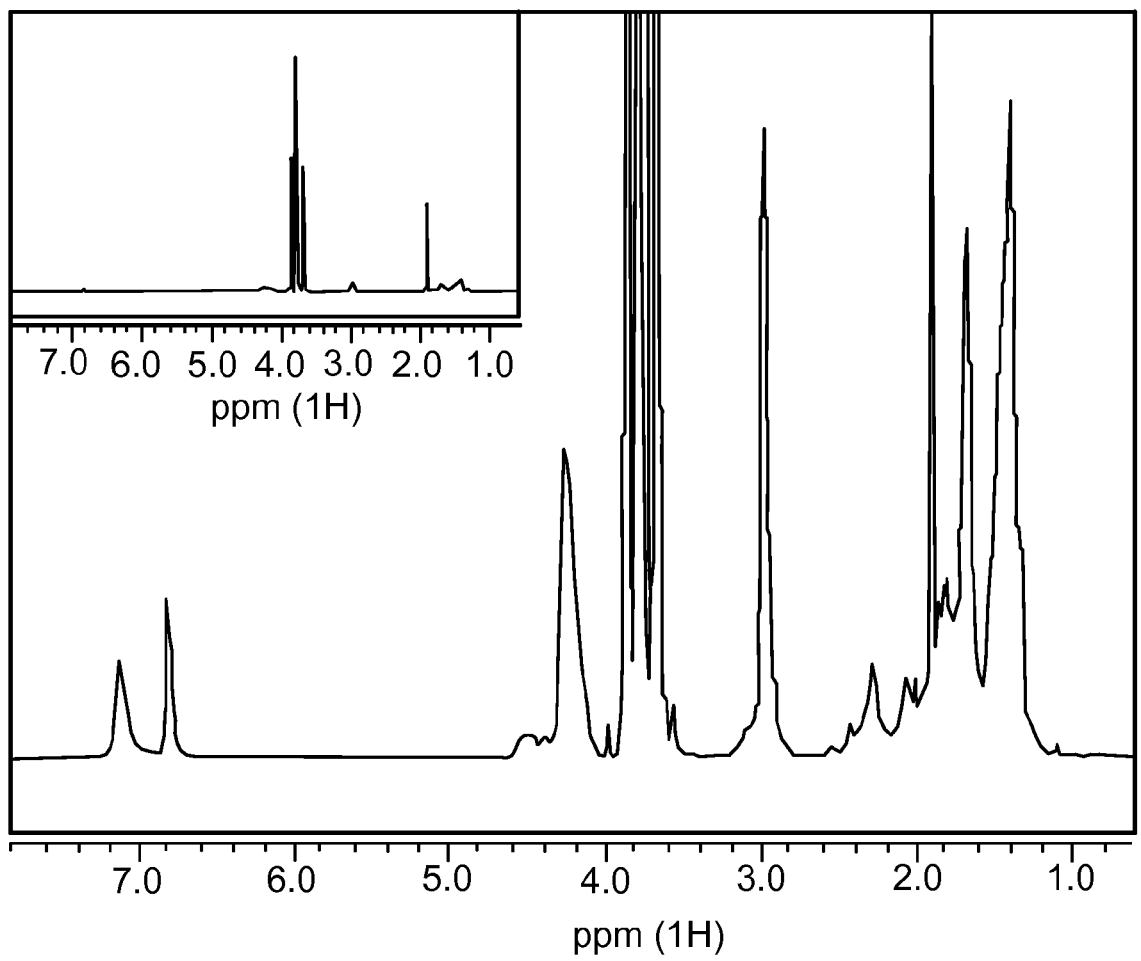
Figure 7:
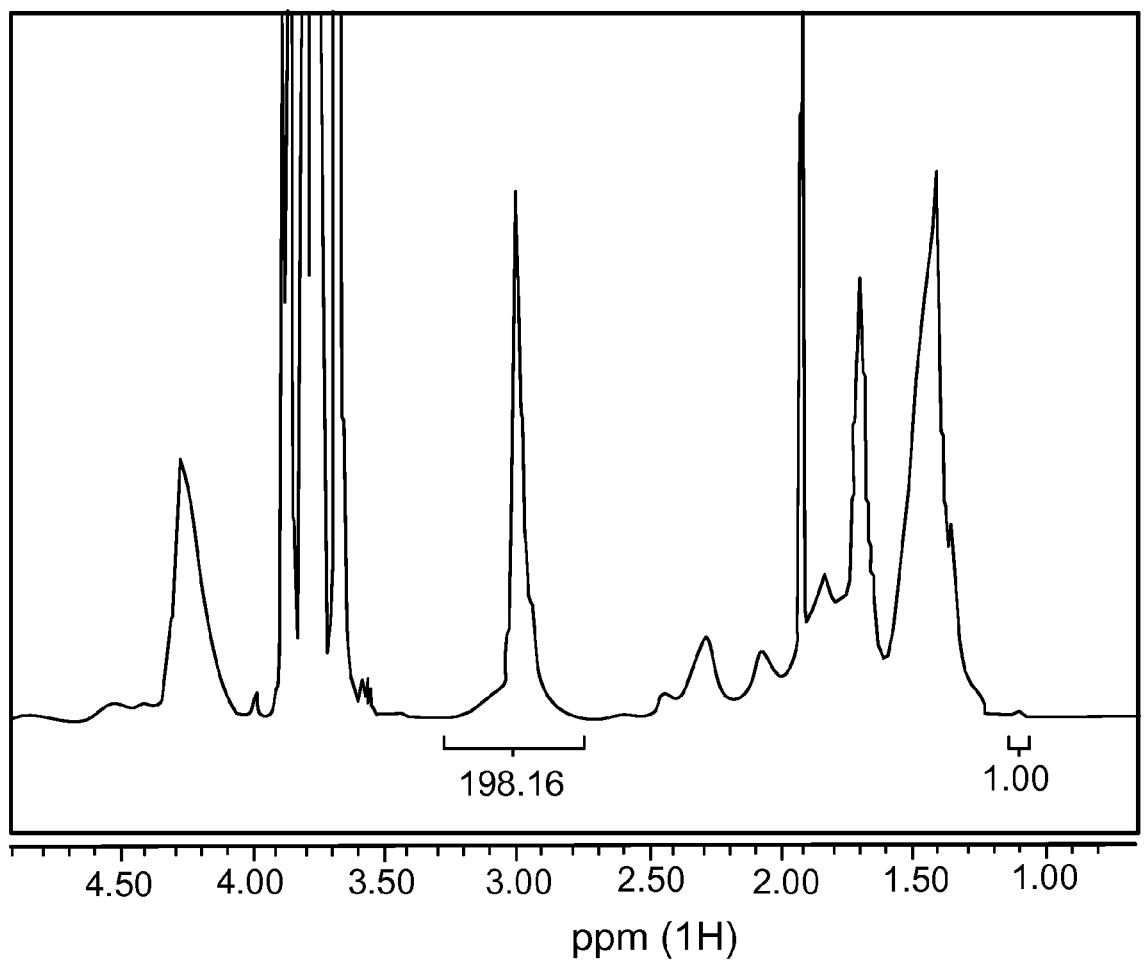
Figure 8A:
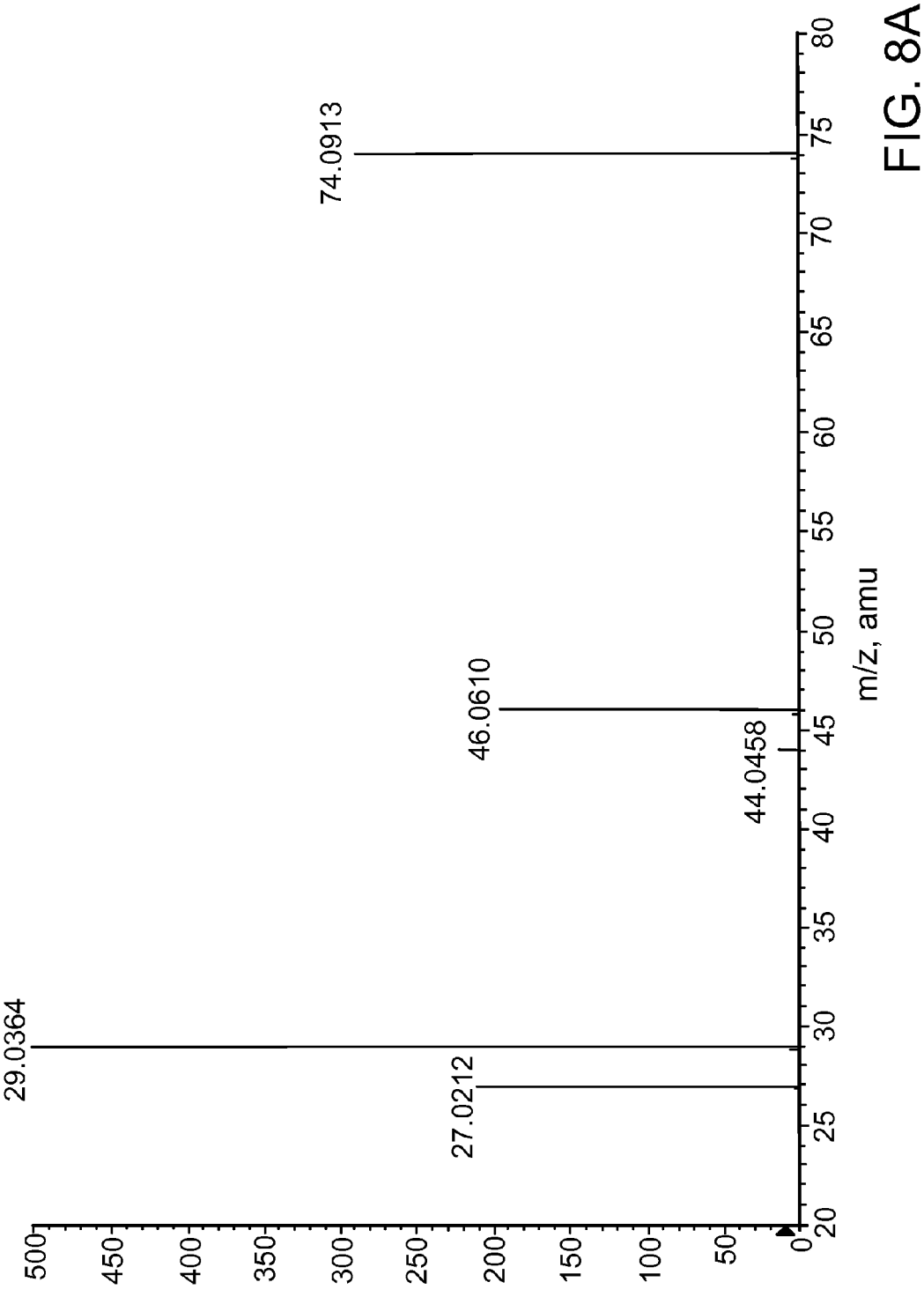
Figure 8B:
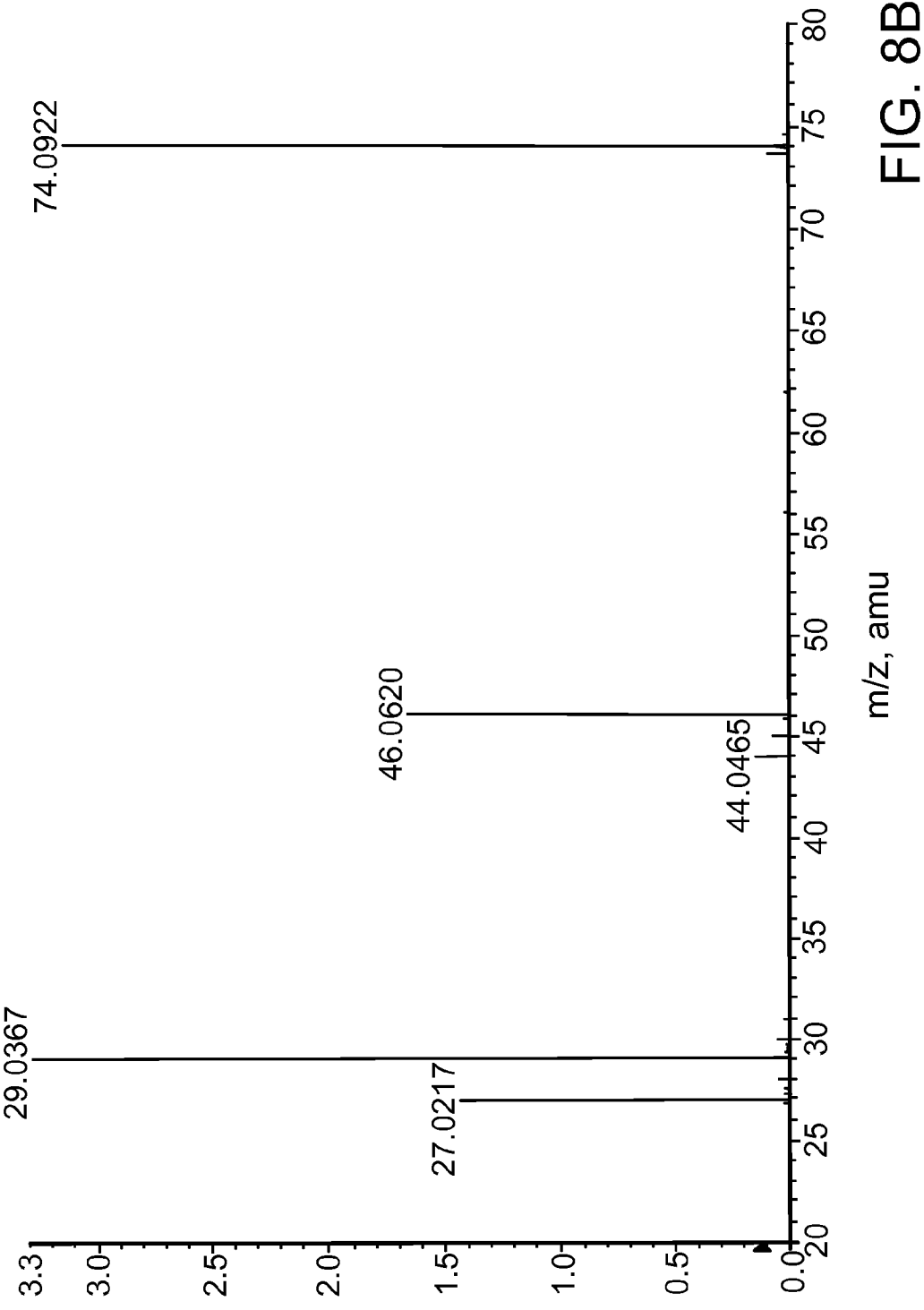

Having thus described the presently disclosed subject matter in general terms, reference will now be made to the accompanying drawings, which are not necessarily drawn to scale, and wherein:

FIG. 1 is a non-limiting graphical illustration depicting a representative process for producing copolymer-1, i.e., glatiramer acetate;

FIG. 2 is a non-limiting graphical illustration depicting representative steps of polypeptide digestion with a protease enzyme, e.g., Glu-C, and peptide separation according to one embodiment of the presently disclosed subject matter, wherein peptides having a C-terminus diethylamide group instead of a carboxyl group are isolated and then analyzed;

FIG. 3 is a non-limiting graphical illustration depicting an amino acid, e.g., alanine, and an amino acid, e.g., alanine, having a C-terminus diethylamide group instead of a carboxyl group;

FIG. 4 is a non-limiting graphical illustration of a method of purifying polypeptides, e.g., glatiramer acetate, having a diethylamide group at the C-terminus of an amino acid instead of a carboxyl group;

FIG. 5 is a non-limiting graphical illustration depicting the 600 MHz 1D $^1$H NMR spectrum of a sample of Ala-Ala dipeptide, wherein one alanine amino acid has a C-terminus diethylamide group instead of a carboxyl group;

FIG. 6 is a non-limiting graphical illustration depicting the 600 MHz 1D $^1$H NMR spectrum of a sample of glatiramer acetate. The inset displays an expansion centered on the methyl resonances of a C-terminus diethylamide moiety;

FIG. 7 is a non-limiting graphical illustration depicting the 1D $^1$H NMR spectrum of a sample of glatiramer acetate after local baseline correction and integration of selected signals;

FIGS. 8A and 8B are non-limiting graphical illustrations depicting representative MS/MS fragmentation patterns of diethylamine generated by fragmentation of a Copolymer-1 sample;

FIG. 8A is a non-limiting graphical illustration of a representative MS/MS fragmentation pattern of diethylamine; and FIG. 8B is a non-limiting graphical illustration of an ion with the same mass as diethylamine generated by in-source fragmentation of a Copolymer-1 sample.

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

All publications, patent applications, patents, and other references are herein incorporated by reference in their entirety, unless otherwise indicated, to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

I. General Considerations

The presently disclosed methods can be used to characterize one or more peptides, peptide mixtures, and/or polypeptide mixtures, including, but not limited to, copolymers, such as a polypeptide mixture comprising a heterogeneous population of polypeptides consisting of alanine, glutamic acid, tyrosine and lysine, e.g., Copolymer-1, also referred to herein as glatiramer acetate, or other polypeptide mixtures having similar properties. As used herein, a "polypeptide" refers to a polymer comprising amino acid residues that are bonded together with amide linkages, which are commonly referred to as peptide bonds. The peptide linkage is made from a bond between a carbonyl group on the C-terminus end of an amino acid and the nitrogen group on the N-terminus end of another amino acid. When many amino acids are linked using these peptide linkages they form polypeptides. The term "mixture" as used herein, for example, as used in the phrase "a polypeptide mixture," refers to, in some embodiments, a mixture of copolymers of the amino acids comprising L-glutamic acid, L-alanine, L-tyrosine, and L-lysine.

As used herein, a "copolymer," "amino acid copolymer," or "amino acid copolymer preparation" is a heterogeneous mixture of polypeptides consisting of a defined plurality of different amino acids (typically consisting of between 2-10, e.g., between 3-6, different amino acids). A copolymer may be prepared from the polymerization of individual amino acids, or may be produced recombinantly. The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. Further, an amino acid copolymer having one or more non-peptide or peptidomimetic bonds between two adjacent residues is included within this definition. A copolymer is typically non-uniform with respect to the molecular weight of each species of polypeptide within the mixture.

In one embodiment of the invention, the amino acid copolymer is a mixture of polypeptides comprising the amino acids Y, E, A, and K; Y, F, A, and K; V, Y, A, and K; V, W, A, and K; V, E, A, and K or F, E, A, and K. In another embodiment of the invention, the amino acid copolymer contains four different amino acids, each from a different one of the following groups: (a) lysine and arginine; (b) glutamic acid and aspartic acid; (c) alanine and glycine; and (d) tyrosine and tryptophan. A specific copolymer according to this embodiment of the present invention comprises a mixture of polypeptides comprising alanine, glutamic acid, lysine, and tyrosine. In one embodiment, the copolymer comprises a mixture of polypeptides consisting of the amino acids Y, E, A, and K, also referred to as Copolymer-1 (Cop 1) or glatiramer acetate. In another embodiment, the amino acid copolymer contains three different amino acids each from a different one of three above mentioned groups (a) to (d), e.g., Y, A, and K; Y, E, and K; K, E, and A; or Y, E, and A.

In another embodiment, the amino acid copolymer comprises amino acids including, but not limited to, alanine-glutamic acid-lysine-tyrosine-alanine (AEKYA), alanine-glutamic acid-lysine-valine-alanine (AEKVA), alanine-glutamic acid-lysine-phenylalanine-alanine (AEKFA), alanine-lysine-tyrosine-alanine-glutamic acid (AKYAE), glutamic acid-alanine-lysine-tyrosine-alanine (EAKYA), alanine-lysine-valine-alanine-glutamic acid (AKVAE), and glutamic acid-alanine-lysine-valine-alanine (EAKVA), alanine-lysine-phenylalanine-alanine-glutamic acid (AKFAE), and glutamic acid-alanine-lysine-phenylalanine-alanine (EAKFA).

The presently disclosed methods are suitable for characterizing complex polypeptide mixtures prepared by any known method in the art. In some processes for producing glatiramer acetate, such as the non-limiting reaction scheme provided in FIG. 1 and related processes known in the art, diethylamide groups are formed during the manufacturing process. In many processes, copolymerization of N-carboxyanhydrides of L-alanine, L-glutamic acid, L-tyrosine, and L-lysine, is initiated by the addition of diethylamine. Without wishing to be bound by any one particular theory, it is thought that during this process, the diethylamine binds covalently to the C-terminus carboxylic acid (after which it is referred to as a diethylamide group or moiety) and remains bound to the end of the polypeptide chains of the protected polypeptides as a result of formation of an amide bond where a carboxyl group otherwise would be present. Amino acids or polypeptide chains having a diethylamide moiety instead of a carboxyl group at one end thereof also are referred to herein as "modified amino acids" or "modified macromolecular chains," respectively.

The diethylamide groups can be formed from any of the four amino acids used to produce glatiramer acetate. Chain depolymerization, for example, by hydrobromic acid/acetic acid, followed by removal of the protecting groups and dialysis or ultracentrifugation does not completely hydrolyze the diethylamide moiety or otherwise remove it from the polypeptide mixture. As a result, two types of C-terminal residues are present in the polypeptide mixture: C-terminal residues of the four natural amino acids, i.e., lysine, tyrosine, glutamic acid, and alanine, having a free carboxyl group and C-terminal residues having a diethylamide group instead of a free carboxyl group.

II. Methods for Evaluating Complex Polypeptide Mixtures

The presently disclosed subject matter provides methods for evaluating or characterizing one or more peptides, peptide mixtures, and polypeptide mixtures, including complex polypeptide mixtures, such as Copolymer-1 and similar complex polypeptide mixtures. In some embodiments, the method includes fractionating the peptide or polypeptide mixture (e.g., separating the mixture into simpler mixtures or enriching certain species in the mixture); detecting the presence of certain macromolecules and/or identifying the macromolecules therein; and optionally quantifying the amount of the certain macromolecules, including modified amino acid structures or macromolecules, such as peptides or polypeptides having a diethylamide moiety instead of a carboxyl group present on at least one end thereof. In some embodiments, the quantifying step can include quantifying the relative mass or molar amount of modified amino acid structures in a polypeptide or polypeptide mixture or the relative molar amount of modified macromolecular chains in a polypeptide mixture.

One embodiment of the presently disclosed subject matter includes a method for assaying a sample selected from the group consisting of Copolymer-I, or fragmented, fractionated, or derivatized Copolymer-I, i.e., a copolymer having an attached chemical moiety on one or more residues in the copolymer, or polymeric precursors (e.g., the intermediates I, II and III shown in FIG. 1) thereof, the method comprising analyzing the sample by a method including, but not limited to, mass spectrometry (MS), liquid chromatography mass spectrometry (LC-MS), nuclear magnetic resonance (NMR) spectroscopy, antibody detection methods, Raman spectroscopy, and capillary electrophoresis.

In some embodiments, the presently disclosed methods include partially or completely depolymerizing the polypeptide sample by a chemical or an enzymatic method, and then analyzing the partially or completely depolymerized sample by a method including, but not limited to, MS, LC-MS, NMR, antibody detection methods, Raman spectroscopy, capillary electrophoresis, liquid chromatography, gas chromatography, and ion chromatography.

One embodiment of the presently disclosed subject matter includes partially or completely depolymerizing the polypeptide sample by a chemical or an enzymatic method, wherein diethylamine is liberated from a polypeptide having a diethylamide group instead of a carboxyl group present on at least one end thereof, and analyzing the partially or completely depolymerized sample by a method including, but not limited to, MS, LC-MS, NMR, antibody detection methods, Raman spectroscopy, capillary electrophoresis, liquid chromatography, gas chromatography, and ion chromatography. In some embodiments, the presently disclosed methods analyze the partially or completely depolymerized sample for diethylamine liberated therefrom.

In some embodiments, the presently disclosed subject matter provides a method of detecting, identifying, and/or quantifying the relative molar amounts of modified amino acids in a polypeptide or polypeptide mixture. In some embodiments, the method can include depolymerizing the polypeptide molecules by enzymatic or chemical digestion. The method also can include determining the molar amount of a C-terminal diethylamide moiety in a polypeptide mixture of glutamic acid, lysine, alanine and tyrosine, such as glatiramer acetate, or the molar amount of liberated diethylamine. The method of analysis can include liquid chromatography, gas chromatography, ion chromatography, mass spectrometry, liquid chromatography mass spectrometry, NMR, antibody methods, Raman spectroscopy, and capillary electrophoresis, preferably multidimensional NMR spectroscopy.

In one embodiment, the presently disclosed subject matter provides a method of analyzing a sample of Copolymer-1 or a polymeric precursor thereof (e.g., intermediate-I, intermediate-II, and intermediate III as shown in FIG. 1), the method including contacting an antibody or antigen binding portion thereof, wherein the antibody or antigen binding portion thereof specifically binds to either a diethylamide structural moiety or to a particular peptide, with a Copolymer-1 sample or polymeric precursor thereof, under conditions to permit binding, thereby allowing analysis, for example, quantitative analysis, of the diethylamide structural moiety in the Copolymer-1 sample, or amino acid residues or polypeptide chains having a diethylamide moiety at one end thereof. In another embodiment, the method includes determining the presence of a diethylamide moiety by detecting an antibody or antigen binding portion thereof bound to the diethylamide moiety. In some embodiments, the antibody can be absorbed on or otherwise attached, e.g., by a linking group, to a surface. In some embodiments, the antibody can be tagged with a label, such as a fluorescent label or a radioisotope label.

In another embodiment, the sample, e.g., a Copolymer-1 sample, can be a size fractionated sample. The method can further include analyzing one or more fractions of the sample to detect the presence of a diethylamide structural moiety without isolating the species that includes the diethylamide moiety. In some embodiments, the presently disclosed subject matter includes determining the amount and/or the size distribution of the diethylamide structural moiety. In another embodiment, the method further includes classifying, selecting, or discarding the sample based at least, in part, upon the determination of the diethylamide structural moiety, e.g., the total percentage of peptide chains having a C-terminus diethylamide group instead of a carboxyl group at one end thereof. In some embodiments, this determination can be based on an absolute value, whereas in other embodiments, this determination can be based on a comparison of the sample under test to a reference standard.

In another embodiment, the presently disclosed subject matter provides a method of assaying a reference standard for a composition, e.g., a drug, by analyzing a sample, e.g., a composition of mixed peptides, such as Copolymer-1 or more particularly COPAXONE®, and determining if a diethylamide structural moiety or mixture of diethylamide structural moieties is present in the reference standard. In some embodiments, the presently disclosed method evaluates a value or parameter, wherein the value or parameter represents the presence, size distribution, and/or quantity of a diethylamide structural moiety. More particularly, the presently disclosed methods can be used to determine the molar amount of a peptide or polypeptide having a diethylamide group instead of a carboxyl group present at the C-terminus in a polypeptide mixture of glutamic acid, lysine, alanine and tyrosine, such as glatiramer acetate. In some embodiments, the method does not require the isolation of the species being evaluated.

In one embodiment, the presently disclosed subject matter provides a method of testing a preparation of a copolymer, such as Copolymer-1, for the presence and/or amount of modifications or modified groups at the carboxyl-terminus of polypeptide chains of the copolymer, e.g., for the presence or amount of a diethylamide moiety at the C-terminus thereof or for diethylamine liberated from such polypeptides. The method includes evaluating the amount of diethylamide moieties, or amino acid residues, peptides, or polypeptide chains having a diethylamide moiety at one end thereof, in a sample copolymer preparation, and comparing the amount of diethylamide moieties in the preparation to a reference value, e.g., a specification value or a control value, or to a value obtained from a direct measurement of a reference copolymer preparation. The sample preparation can be, for example, Copolymer-1 or a polymeric precursor thereof, including fragmented, fractionated or derivatized Copolymer-1, or polymeric precursors thereof (e.g., intermediate-I, intermediate-II, and intermediate III as shown in FIG. 1). The method also can include a step of disposing of (i.e., determining the fate of) the preparation based on the evaluation (e.g., a step of determining whether or not the preparation is suitable for pharmaceutical use, a step of determining whether or not the preparation is suitable for subjecting to further process steps (e.g., in a manufacturing process for copolymer-1), or a step of releasing the sample preparation for pharmaceutical use at least partly based on the evaluation).

In one embodiment, the reference value is a predetermined value, e.g., a pharmaceutical specification value for glatiramer acetate, which, in some embodiments can be between about 7 and about 20 mole percent of polypeptides, e.g., 7, 8, 9, 10, 11, 12, 13, 14, 15, 16, 17, 18, 19, and 20 mole percent of polypeptides, including intermediate values, e.g., 7.5, 8.5, 9.5, 10.5 mole percent, and the like; in some embodiments, between about 8 and about 18 mole percent of polypeptides; in some embodiments, between about 10 and about 15 mole percent of polypeptides, in some embodiments, between about 12 and about 14 mole percent of polypeptides, and, in some embodiments, about 13 mole percent of polypeptides.

In another embodiment, the value is a predetermined value corresponding to the amount of polypeptides having a diethylamide moiety instead of a carboxyl group at one end thereof in a reference preparation, e.g., a Copolymer-1 precursor preparation (e.g, intermediate-I, intermediate-II, and intermediate III as shown in FIG. 1). In some embodiments, a reference Copolymer-1 precursor preparation has between about 60% and about 100%, e.g., 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.9, and 100%, diethylamide moieties (mole percent of polypeptides); in some embodiments, between about 75% and about 100%; and in some embodiments, greater than about 60%, 70%, 75%, 80%, 85%, 90%, or 95% diethylamide moieties (mole percent of polypeptides). The total percentage of peptide chains having a diethylamide group at an end thereof present in the polypeptide mixture under test can be reported as an absolute percentage or as a percentage relative to a reference standard, e.g., a sample of glatiramer acetate having known properties. These values also can be reported in other ways, e.g., as mole % of residues, or weight percent (ppm), by applying appropriate conversion factors known in the art.

In one embodiment, an amount of polypeptides having a diethylamide moiety at one end thereof in a sample preparation can be evaluated by a technique including, but not limited to, one-dimensional (1D) $^1$H NMR; chemical depolymerization followed by detection of liberated diethylamine, wherein the detection is by, for example, gas chromatography or LC-MS; chemical or proteolytic digestion followed by HPLC; or by liberating diethylamine and derivatizing the diethylamine with a chromophore before detection by HPLC.

In another embodiment, the presently disclosed subject matter provides a Copolymer-1 preparation (e.g., a glatiramer acetate preparation), having between about 7% and about 20% diethylamide moieties (mole percent of polypeptides), e.g., 7, 8, 9, 10, 11, 12, 13, 14, 15, 16, 17, 18, 19, and 20% diethylamide moieties (mole percent of polypeptides); in some embodiments, between about 8% and about 18% diethylamide moieties (mole percent of polypeptides); in some embodiments, between 10% and 15% diethylamide moieties (mole percent of polypeptides); in some embodiments, between 12% and 14% diethylamide moieties (mole percent of polypeptides); and, in some embodiments, about 13% diethylamide moieties (mole percent of polypeptides). In one embodiment, the Copolymer-1 preparation is a pharmaceutical preparation, e.g., a pharmaceutical preparation of glatiramer acetate having an average molecular weight (peak maximum) of less than about 13,000, 13,100, 13,200, 13,300 and/or 13,400 Daltons, see International PCT Patent Publication No. WO 2006/029411, page 55, line 25, to page 56, line 8, and pages 60-63.

The ability to characterize such polypeptide mixtures can be used to monitor or ensure batch-to-batch consistency or quality during a preparation process and to monitor or evaluate the similarity of a particular polypeptide mixture to a reference material from a structure-activity perspective, for example, to evaluate or ensure biological equivalence of a sample under test, and/or as part of a release test.

II. General Methods for Evaluating or Characterizing Complex Polypeptide Mixtures In some embodiments, the presently disclosed methods for characterizing a complex polypeptide mixture include one or more of the following steps: fragmenting, or depolymerizing, the polypeptides comprising the complex polypeptide mixture; separating the peptides, polypeptides, or fragments thereof; detecting and/or quantifying the peptides, polypeptides or fragments thereof; and purifying the peptides, polypeptides, or fragments thereof Non-limiting, representative embodiments of these individual steps are provided herein below.

A. Fragmentation

In some embodiments, polypeptide molecules present in a complex mixture can be fragmented or cleaved into smaller fragments of polypeptides by any known method known in the art, including chemical, enzymatic, or physical methods. Cleavage generally refers to scission of a chemical bond within a protein, peptide, or polypeptide to produce protein, peptide, or polypeptide "fragments." in some embodiments, fragmentation of protein molecules, peptides, or polypeptides in a complex mixture, can be accomplished using chemical agents including, but not limited to, a strong acid, e.g., 6N hydrochloric acid, a mild acid, e.g., 70% formic acid at 40° C., hydroxylamine, a strong base, e.g., 1N sodium hydroxide, cyanogen bromide, iodosobenzoic acid, or 2-nitro-5-thiocyanobenzoate followed by use of alkali base. The chemical fragmentation also can include chemical agents used for Edman degradation techniques, such as phenylisothiocyanate and other such agents known in the art.

Further, the fragmentation agent can be a proteolytic enzyme. Fragmentation can be accomplished using one or more proteases, including trypsin, chymotrypsin, elastase, ficin, papain, pepsin, plasmin, thermolysin, endopeptidase, proteinase K, Ox Bile, Lemon Pectin, Horseradish Peroxidase, gluc-C, endo lys-C, carboxypeptidase, calpain, and subtilisin. The use of more than one protease enzyme can generate overlapping fragments. The proteolytic agent can be free in solution, or immobilized in or on a support. Protease enzymes suitable for use with the presently disclosed methods can be isolated from any organism, including, but not limited to *Lactobacillus acidophilus, Bifidobacterium bifidum, Lactobacillus bulgaricus, Streptococcus thermophilus,* and *Lactobacillus casei.*

In another embodiment, the protein, peptide or polypeptide can be fragmented using a physical technique, including, but not limited to, boiling, sonication, or shearing.

B. Separation

In some embodiments, the polypeptides or fragmented polypeptides present in the complex mixture can be separated whereby the polypeptides or fragmented polypeptides are isolated into subpopulations of macromolecules. The separation can be based on a property shared by a class of macromolecules within the complex mixture, for example, size, charge, hydrophobicity, or any of the properties of macromolecules described herein. More particularly, the macromolecules, or fractions of macromolecules, in a complex mixture can be isolated from the other macromolecules in the mixture based on, for example, migration rates through a gel; size; molecular weight; migration in response to an applied electrical field; charge; hydrophobicity; boiling point, solubility, e.g., through solvent extraction; precipitation; affinity; phosphorylation; or the presence of low abundance amino acid residues, such as tyrosine. Accordingly, the separation can be based on any chemical, physical or functional property shared by a population of macromolecules within the complex mixture, or by the cleaved moiety of interest, e.g., diethylamine.

In some embodiments, a single separating step can be used. In other embodiments, one or more separating steps can be used. One of ordinary skill in the art can use any separation techniques in any combination and in any order to separate the desired macromolecules from the remainder of the macromolecules in the complex mixture. Further, the separation techniques can be performed as a single, one-dimensional method or as a multidimensional method. The separation techniques can be performed using gels or chromatography methods. The separation step, e.g., an electrophoretic separation method, can be performed under native or denaturing conditions (e.g., sodium dodecyl sulfate (SDS) or urea). Examples of non-limiting separation techniques are provided immediately herein below. The following examples can be used in accordance with the presently disclosed methods. These examples are provided to facilitate understanding of the presently disclosed methods and in no way are meant to limit the scope of the claimed subject matter.

1. Gel Electrophoresis

The methods for separation can be based on mobility of macromolecules through a matrix or gel. Gel electrophoresis provides separation and/or visualization of the macromolecules and permits determination of certain properties of a macromolecule, including its isoelectric point and/or approximate molecular weight.

For macromolecules that are proteins, peptides, polypeptides, or fragments thereof, the amino acid sequence, the number of amino acids, and/or the different R-groups can dictate the properties of molecular weight and/or overall (net) charge. If the protein, peptide, polypeptide, or fragment thereof, has more positively charged amino acids, such that the sum of the positive charges exceeds the sum of the negative charges, the protein, peptide, polypeptide, or fragment thereof will have an overall positive charge and migrate toward a negatively charged electrode in an electrical field. Proteins, peptides, polypeptides, or fragments thereof having a variation of one amino acid have a different overall charge, and thus are electrophoretically distinguishable.

Sodium dodecyl sulfate (SDS) is an anionic detergent that binds to most soluble proteins or peptides in aqueous solutions over a wide pH range. Proteins or peptides bind amounts of SDS in proportion to the size of the protein or peptide molecule. A polyacrylamide gel with an acrylamide content above a critical density restrains larger molecules from migrating as fast as smaller molecules. Because the charge-to-mass ratio is nearly the same among SDS-denatured proteins or peptides, the final separation of proteins or peptides primarily depends on the differences in molecular weight (MW) of the proteins or peptides. Protein or peptide separation by SDS-PAGE gel electrophoresis can be used to determine the relative abundance of proteins or peptides in a sample (e.g., a sample from a complex mixture), their approximate molecular weights, and in what fractions they can be found. Further, the purity of proteins or peptides in a sample can be assessed with this technique. Different staining or affinity procedures can be used to detect rare proteins and characterize their biochemical properties. Specialized techniques such as Western blotting, two-dimensional electrophoresis, and peptide mapping also can be used.

2. Size

In some embodiments, the separation method can be based on based on size, molecular weight, or molar mass and can be accomplished using size exclusion chromatography (SEC), gel permeation chromatography (GPC), or gel filtration chromatography (GFC).

In SEC, a mobile phase comprising a solvent and a portion of the protein, peptide, polypeptide, or fragment thereof disposed therein flows past a stationary phase. The stationary phase, through a physical and/or a chemical interaction with the protein, peptide, polypeptide, or fragment thereof, temporarily retains some portion of the protein, peptide, polypeptide, or fragment thereof and thereby separates that portion of the protein, peptide, polypeptide, or fragment thereof from other macromolecules in the mobile phase. The stationary phase typically comprises finely divided, porous particles, such as microporous crosslinked agarose-based gels, modified polymethylmethacrylate gels, or porous silica. Protein, peptide, or polypeptide molecules that are smaller than the pore sizes in the particles can enter the pores and therefore have a longer path and longer transit time than larger molecules that cannot enter the pores. Thus, larger molecules elute earlier in the chromatogram, while smaller molecules elute later.

Components of an SEC system can include: one or more pumps for maintaining constant, pulseless rates of flow; column types for the molecular weight range of interest; and a detector system for detecting and/or quantifying the result. Detector systems can be classified as either mass concentration sensitive or molar concentration sensitive. For example, a refractive index detector measures the change in refractive index as the concentration of protein in the solution changes. Another group of molar concentration methods involves the input of ultraviolet light, with the output being fluorescence or absorption by the protein. Other methods include a density detector and an evaporative light-scattering detector.

3. Chromatography Procedures

The methods for separation can be based on other chromatography procedures, including: gas chromatography (e.g., gas-liquid chromatography); gas-solid chromatography; ion chromatography, partition chromatography; adsorption chromatography; thin-layer chromatography; and supercritical fluid chromatography.

4. Capillary Electrophoresis:

The methods for separation can be based on migration of the macromolecules through a medium in response to an applied electrical field (e.g., electrophoresis). In one example, capillary electrophoresis can be used to separate both charged and uncharged macromolecules (e.g., proteins and fragments thereof) ranging in size.

Most molecules of biological interest are charged and thus can be separated by electrophoretic methods. This characteristic is especially true for the diethylamide groups of the peptide fragments which, when placed in the appropriate environment, are charged. In one alternative embodiments, a fused-silica tubing having a length ranging from about 50 cm to about 100 cm and an inside diameter ranging from about 10 $\mu$m to about 200 $\mu$m can be used. Electrodes that can be used vary from 10 to 50 kV. To quantify the amount of peptide or polypeptide chains having a diethylamide group at an end thereof in a sample, with or without purification of the C-terminus end as described above using a method like affinity chromatography, the sample is separated by capillary electrophoresis. Upon separation the detector can be used to determine the presence of the diethylamide groups and determine the amount of peptide or polypeptide chains having a diethylamide group at an end thereof present in the sample.

Capillary electrophoresis encompasses a family of related separation techniques that use narrow-bore fused-silica capillaries to separate a complex mixture. High electric field strengths are used to separate molecules based on differences in charge, size and hydrophobicity. Sample introduction is accomplished by immersing the end of the capillary into a sample vial and applying pressure, vacuum or voltage. Depending on the types of capillary and electrolytes used, the technology of CE can be segmented into several separation techniques including, but not limited to, Capillary Zone Electrophoresis (CZE), Capillary Gel Electrophoresis (CGE), Capillary Isoelectric Focusing (CIEF), Isotachophoresis (ITP), Electrokinetic Chromatography (EKC), Micellar Electrokinetic Capillary Chromatography (MECC OR MEKC), Micro Emulsion Electrokinetic Chromatography (MEEKC). Non-Aqueous Capillary Electrophoresis (NACE), and Capillary Electrochromatography (CEC).

5. Charge

The methods for separation can be based on charge selection, including ion exchange chromatography and cationic chromatography. In ion exchange chromatography, charged substances are separated via column materials that carry an opposite charge. The ionic groups of exchanger columns are covalently bound to the gel matrix and are compensated by small concentrations of counter ions present in the buffer. When a sample is added to the column, an exchange with the weakly bound counter ions takes place. In some embodiments, ion chromatography can be used to detect one or more diethylamine moieties released from a polypeptide structure by chemical cleavage.

6. Hydrophobicity

The methods for separation can be based on hydrophobicity selection, including hydrophobic interaction chromatography, reversed phase chromatography (RPC), or RP-HPLC. Compounds adhere to reversed phase HPLC columns in a high aqueous mobile phase, and are eluted from RP-HPLC columns with a high organic mobile phase. In RP-HPLC compounds are separated based on their hydrophobic character.

The most common RP-HPLC columns are packed with silica particles. The beads or particles are generally characterized by particle and pore size. In one embodiment, particle sizes generally range from about 3 $\mu$m and about 50 $\mu$m, with 5-$\mu$m particles being the most widely used for proteins. The particle pore size is measured in angstroms and generally ranges from about 100 Å to about 1000 Å. In one embodiment, the stationary phase is generally made up of varying lengths of hydrophobic alkyl chains that interact with the analyte. The commonly-available columns for separating macromolecules include, but are not limited to, alkyl chains having C-4, C-8, or C-18 lengths. A C-4 column is generally used to capture larger proteins, and a C-18 column is generally used to capture small proteins or small molecules. In general, reversed phase solvents are used regardless of the hydrophilic or hydrophobic nature of the protein molecules.

7. Solvent Extractions

The separation method can be based on solvent extraction. Solvent extraction involves partitioning a macromolecule between two solvents or a solvent and a solid phase. Because macromolecules having different solubilities in the two phases are distributed differently between the two phases, extraction and/or enrichment of the macromolecules is possible. A macromolecule can be separated based on its own hydrophobic/hydrophilic characteristics and that of the two phases used. The solvent extraction procedures can use any solvent suitable for use in separating macromolecules, such as polypeptides.

8. Precipitation

The separation method can be based on precipitation procedures, which also depends on the solubility of the macromolecules. For example, proteins, peptides, or polypeptides that are soluble in water-based solutions have hydrophilic amino acids on their surfaces that attract and interact with water molecules. This solubility is a function of the ionic strength and pH of the solution. Proteins, peptides, and polypeptides have isoelectric points at which the charges of their amino acid side groups balance each other. If the ionic strength of a solution is either very high or very low, the proteins, peptides, or polypeptides will tend to precipitate at their isoelectric point. Thus, solubility also is a function of ionic strength.

9. Affinity

The separation method can be based on affinity selection of a subset of macromolecules in the sample. Affinity selection includes immuno-affinity using polyclonal and/or monoclonal antibodies, and/or immobilized metal affinity chromatography. The affinity selection method also includes: cysteine affinity using an acylating reagent; or affinity for histidine, carbohydrates and/or phosphate moieties.

Affinity chromatography relies on the protein, peptide, or polypeptide binding specifically to an immobilized ligand while the remainder of the protein, peptide, or polypeptide passes through the column. Any ligand can be used including any chemically generated ligand or a biological molecule, such as a sugar or protein molecule. Suitable ligands also include monoclonal or polyclonal antibodies.

10. Phosphorylated Proteins

The separation method can be based on selection of phospho-peptides, including procedures that use antibodies that react with phosphorylated amino acids (e.g., phosphotyrosine and phosphoserine). Other methods include using gallium loaded immobilized metal affinity chromatography (IMAC) columns, anion exchange chromatography, or zirconia-containing chromatography.

11. Low Abundance Amino Acids

The separation method can be based on selection of peptide molecules comprising certain low-abundance amino acids, such as tyrosine. For example, protein, peptide, or polypeptide molecules comprising tyrosine can be selected using diazonium salts. Protein peptide, or polypeptide molecules comprising tryptophan can be derivatized with 2,4-dinitrophenylsulfenyl chloride at pH 5.0 and selected with an antibody reactive with the 2,4-dinitrophenol. Methods for separating protein, peptide, or polypeptide molecules comprising histidine include acetylation of primary amino groups and selection on immobilized metal affinity chromatography (TMAC) columns loaded with copper.

C. Detection and/or Quantification

The detection and quantification (collectively referred to herein as an "evaluation step") is an analysis of the complex mixture or fractions of the complex mixture, resulting in the generation of qualitative or quantitative data regarding the same. The evaluating step can include any of the procedures described herein below, alone or in combination, and in any order, and can include: gel electrophoresis; amino acid composition analysis; amino acid sequencing (e.g., N-terminal sequencing); sugar analysis; sugar sequencing; fluorescence spectroscopy; mass spectrometry, such as MALDI MS (matrix assisted laser desorption ionization mass spectrometry); MS/MS; NMR; MALDI TOF/TOF; electrospray ionization (ESI); quadrupole; ion trap; magnetic sector or ion cyclotron resonance mass analysis; orthogonal digestion analysis; CE and/or HPLC quantification; infrared spectroscopy; UV-vis spectroscopy; atomic absorption spectroscopy; Raman spectroscopy; X-ray spectroscopy; thermal procedures; potentiometry; and/or electron microscopy. More particularly, the analytical method includes, but is not limited to, mass spectrometry, liquid chromatography mass spectrometry, NMR, antibody detection methods, Raman spectroscopy, and capillary electrophoresis.

1. Mass Spectrometry

The evaluating step can include mass spectral and/or tandem mass spectrometry (MS/MS) techniques. In this technique, parent molecular polypeptide ions are fragmented into smaller ions which are selected and further fragmented to yield information relating to the nature of the peptide mixture. To characterize a type of peptide mixture by mass spectrometry, a type of peptide or a particular segment of a type of peptide can be given positive and negative charges, or ionized, and volatilized in a mass spectrometer. The ionized, volatilized peptide molecules or segment thereof can then analyzed by the mass spectrometer, which produces a mass spectrum of the peptide molecule or segment.

A mass spectrometer determines the weight of peptide molecules and segments of peptide molecules, when a peptide molecule or segment is analyzed, the information provided by mass spectrometry can be of use in inferring the sequence of amino acid residues in the peptide molecule or segment. Mass spectrometers also are sensitive enough to provide information about modifications to particular amino acid residues of a peptide molecule or segment. Methods such as matrix assisted laser desorption ionization (MALDI) and electrospray ionization (ESI) and nanospray GC/MS, LC/MS, MS/MS, LC MS/MS, SIMS, Fourier transform instruments, a laser microprobe mass spectrometry, gas phase and desorption instruments, mass spectrometry that involves electron ionization (EI), chemical ionization (CI), field ionization, field desorption, fast atom bombardment, plasma desorption, thermal desorption, electro hydrodynamic ionization, and thermospray ionization are all encompassed within the meaning of mass spectrometry.

2. NMR Spectroscopy

The evaluation step can include nuclear magnetic resonance (NMR) spectroscopy. NMR is a phenomenon that occurs when the nuclei of certain atoms are immersed in a static magnetic field and exposed to a second oscillating magnetic field. Some nuclei experience this phenomenon, and others do not, dependent upon whether they possess a property called spin. Thus, NMR spectroscopy can be used to study the chemical structure for many molecules possessing a spin characteristic.

Suitable NMR techniques include, but are not limited to, $^1$H, $^2$H, $^{23}$Na, $^{15}$N, $^{13}$C, and $^{18}$O. More than 200 isotopes have magnetic moments and can be studied using NMR. NMR can be done in the solution and solid states, and all types of NMR experiments are within the scope of the presently disclosed subject matter including broad band decoupling, off-resonance decoupling, nuclear Overhauser enhancement (NOE), and two dimensional NMR (2D-NMR). Representative examples of NMR methods include, but are not limited to: one pulse experiments; spin decoupling and difference spectroscopy; multiple pulse experiments, including simples echoes, J-modulation, population transfer, selective polarization transfer, non selective polarization transfer-INEPT, inverse INEPT, Refocused INEPT; 2D-NMR, including a basic 2 dimension sequence, methods involving removing heteronuclear and/or homonuclear coupling; inverse-detected spectra-HMQC, homonuclear shift correlation experiments-COSY; variations on COSY, multiple quantum coherence-INADEQUATE, spin locked sequences-TOCSY, solvent suppressed two-dimensional spectroscopy, three dimensional NMR (3D-NMR); methods studying connections through bonds; methods studying connections through space, e.g., NOE experiments, including NOESY and ROESY; and methods measuring relaxation rates, including inversion recovery, saturation recovery, and progressive saturation.

The presently disclosed NMR methods optionally can include methods for suppressing signals arising from solvents, buffers, and/or contaminants, including, but not limited to, presaturation or flip-back techniques.

3. Infrared Spectroscopy

The evaluation step can be Infrared spectroscopy (IR Spectroscopy), including Fourier transform infrared (FTIR) spectroscopy. IR spectroscopy is a type of spectroscopy that uses the infrared portion of the electromagnetic spectrum and can be used to investigate the composition of a sample, as well as detailed chemical information on the structures of biomolecules. When performed in a time-resolved fashion, the structural intermediates in biological reactions also can be examined. To measure a sample, a beam of monochromatic infrared light is passed through the sample, and the amount of energy absorbed at different frequencies, or wavelengths of IR radiation, is recorded. The position of the IR absorption peaks can be related to specific types of chemical bonds have specific frequencies at which they vibrate. Within the meaning of infrared spectroscopy, the invention also includes all forms of infrared spectroscopy including, but not limited to, internal reflection infrared spectroscopy, photoacoustic infrared spectroscopy, near-infrared spectroscopy, near infrared reflectance spectroscopy, far-infrared spectroscopy, and infrared emission spectroscopy.

4. Gel Electrophoresis

The evaluation step can include gel electrophoresis. The description of the Gel Electrophoresis step as discussed above is incorporated herein by reference with the intent to apply it to the evaluation step.

5. Emission Spectroscopy

The evaluation step can include emission spectroscopy, which encompasses molecular fluorescence, phosphorescence, and chemiluminescence. Fluorescence and phosphorescence occur as a result of absorption of photons. Chemiluminescence is based on the emission spectra of excited species formed as a result of a chemical reaction. Measurements of the intensity of fluorescence, phosphorescence, and chemiluminescence characteristics allow quantitative determination of an organic and inorganic species. Generally, the instruments have a source, filters and/or other devices to separate or discriminate between wavelengths, such as a monochromator, detectors, cells and compartments. Some instruments that can be used in fluorescence spectroscopy include fluorometers, fiber-optic fluorescence sensors, spectrofluorometers, and phosphorimeters.

6. UV-Vis Spectroscopy

The evaluation step can include UV-vis spectroscopy, which probes the electronic transitions of molecules as they absorb light in the UV and visible regions of the electromagnetic spectrum. Any species with an extended system of alternating double and single bonds will absorb UV light, and anything with color absorbs visible light, making UV-vis spectroscopy applicable to a wide range of samples. With regard to instrumentation, the light source is usually a hydrogen or deuterium lamp for UV measurements and a tungsten lamp for visible measurements. The wavelengths of these continuous light sources are selected with a wavelength separator, such as a prism or grating monochromator. Spectra are obtained by scanning the wavelength separator and quantitative measurements can be made from a spectrum or at a single wavelength. A variety of UV-vis spectroscopy methods exist. These methods include, but are not limited to: molecular Ultraviolet/Visible, Absorption Spectroscopy, Ultraviolet spectroscopy, Ultraviolet/Visible Absorption Spectroscopy.

7. Raman Spectroscopy

Raman Spectroscopy can be used to quantify the amount of peptide or polypeptide chains having a diethylamide group at an end thereof in a sample. The advantage of Raman spectroscopy is that water does not give rise to a Raman signal. Raman intensities are directly proportional to the concentration of the measured species. In this regard, Raman spectroscopy can be used to determine the concentration of a particular species present.

During Raman excitation, the change in relative values of the Raman peak areas arising from molecular vibrations can be used as a measure of the percentage of various structures present within a sample, for example a purified sample. Upon purification of the C-terminus end as described hereinabove using a separation method, such as affinity chromatography, the isolated C-terminus peptide can be analyzed using Raman Spectroscopy. Raman peaks corresponding to the groups that make up the diethylamide groups are readily apparent during Raman Spectroscopy. Various kinds of Raman techniques can be used to analyze the diethylamide groups. A representative sample includes conventional Raman spectroscopy, resonance Raman spectroscopy and surface-enhanced Raman spectroscopy.

8. Antibody Detection Methods

An antibody specific for a selected structure (or specific for the other structures in a sample) can be used to determine the presence and/or amount of a selected structure in a sample, e.g., an amount of peptide or polypeptide chains having a diethylamide group at an end thereof present in a sample of Copolymer-1 or COPAXONE®. For example, an antibody specific to the modified or unmodified C-terminus, N-terminus or internal peptide groups are readily available or can be grown by methods known in the art.

For example, to determine the amount of peptide or polypeptide chains having a diethylamide group at an end thereof present, with or without purification of the C-terminus peptides as described hereinabove using a separation method, such as affinity chromatography, the purified C-terminus peptides can be incubated with a preselected antibody for a period of time, e.g., two hours, at room temperature. The antibody will only bind chains specific for the modified structure to which it was raised, e.g., the C-terminus peptides. The antibody also can include a tag that fluoresces when exposed to electromagnetic radiation. After a period of time, e.g., two hours, excess antibodies are washed off and the sample is purified and optionally quantified.

The purified sample is then exposed to electromagnetic radiation which causes the bound antibodies to fluoresce. The amount of fluorescence is proportional to the amount of diethylamide groups present on the C-terminus peptides.

D. Purification

The purification step, alternatively referred to herein as an enriching step, produces a fraction of macromolecules having a greater proportion of selected macromolecules. The fraction of macromolecules resulting from the purification step can include macromolecules other than the selected macromolecules. Any of the above-described separation methods can be used for the purification step. The description of the separation step disclosed hereinabove is incorporated herein by reference with the intent to apply these techniques to the purification step.

In some embodiments, purification of the peptide or polypeptide chains having a diethylamide group at an end thereof can be achieved by any method known in the art. One method of purification is shown in FIG. 4. More particularly, Copolymer-1 can be treated with an alcohol, resulting in transesterification of the carboxylate groups. Alternately, copolymer-1 can be treated with EDC/amine chemistry. Treatment with either of these chemistries results in the carboxylate groups on the glutamic acid and the C-terminus end of the polypeptide being capped. Other purification methods also are known in the art. For example, Copolymer-1 can be treated with a protein that binds to the carboxylate groups, e.g., biotin. Whether achieved by chemical or biological means, this modified copolymer can then be depolymerized by any method known in the art, such as chemical or an enzymatic digest. This digest produces three types of structures N-terminal peptides, internal peptides and C-terminal peptides.

To purify the C-terminus peptides, methods such as antibody treatment or affinity chromatography can be used. The N-terminal peptides, internal peptides and C-terminal peptides are placed in an affinity chromatography column. The conditions and column are chosen so that the modified N-terminal peptides and internal peptides bind to the column. The C-terminal peptides elute through the column with the mobile phase. The mobile phase is then removed resulting in the purified C-terminal peptides. The purified C-terminal peptides can then be quantified and analyzed by any method known in the art.

In addition, the purification step can include linking the protein, or fragment thereof, to an affinity tag. The affinity tags can be added to the N-terminal or C-terminal end of the protein. Affinity tags include: histidine (His) tags; glutathione-S-transferase (GST) tags; V5 tags; FLAG tags; influenza hemagglutinin (HA) tags; Myc tags; VSV-G tags; thioredoxin (Trx) tags. Other protein tags having affinity for a ligand include: lysine-specific tags, biotin, streptavidin, maltose binding protein (MBP); S-tag; Lex A DNA binding domain (DBD); GAL4 DNA binding domain; herpes simplex virus (HSV), and BPI 6 protein.

III. Application of the Presently Disclosed Methods to Evaluating or Characterizing Complex Polypeptide Mixtures The fragmentation, separation, detection and/or quantification, and purification methods disclosed immediately hereinabove can be applied to the characterization of complex polypeptide mixtures.

A. Fragmentation followed by MS or LC/MS

In one embodiment, the presently disclosed method included detecting non-carboxyl terminal moieties, i.e., diethylamide groups, in a polypeptide mixture using enzymatic depolymerization followed by MS or LC-MS detection. In this embodiment, the polypeptide or polypeptide mixture is depolymerized, preferably by adding one or more proteases to the mixture. Suitable proteases include trypsin, chymotrypsin, elastase, and glu-C, and mixtures thereof. The protease can be selected based on the cleaving properties of the specific protease. For example, trypsin cleaves on the C-terminus of lysine or arginine; chymotrypsin prefers an aromatic side chain on the residue whose carbonyl carbon is part of the peptide bond to be cleaved; and Glu-C cleaves the C-terminus of glutamate. The enzyme/CPX ratio is preferably about 1:50 by weight.

Suitable solvents and buffers can be used during the depolymerization step. For example, for trypsin and Glu-C, preferable solutions include 50-mM ammonium bicarbonate; for digestion with chymotryspin, preferable solutions can include 10-mM Tris-HCl and 10 mM calcium chloride as buffer. Other compatible solvents and buffers known in the art can be used. The depolymerization step, which also is referred to herein as the digestion step, proceeds until the polypeptides are substantially depolymerized into individual peptides. To provide controlled depolymerization, the depolymerization step can occur at an elevated temperature, for example between about 20° C. to about 40° C., over a period of time. In some embodiments, with trypsin the depolymerization occurs at about 37° C. and for chymotrypsin and Glu-C the depolymerization temperature is about 25° C. The depolymerization proceeds until adequate depolymerization occurs, in some embodiments, for at least 12 hours, and in some embodiments, about 16 hours. The digestion can be terminated after suitable digestion has occurred by methods known in the art, such as heating and pH adjustment. In some embodiments, the polypeptides can be denatured by heating or addition of a denaturation solvent prior to depolymerization.

Following depolymerization, the digested polymer fragments comprise N-terminal peptides, internal peptides, and C-terminal peptides, as shown in FIG. 2. These digested polymer fragments can then be isolated using a separation technique. In some embodiments, the peptides are separated using reversed phase high performance liquid chromatography (reversed phase HPLC), wherein the carboxy-terminal fragments are separated from the non-carboxy-terminal fragments, as shown in FIG. 2.

In some embodiments, the mobile phases used in the reversed phase HPLC include water and acetonitrile. A small amount of an acid, such as trifluoroacetic acid (TFA), can be added to both the water and acetonitrile mobile phases. Though not wishing to be bound by any theory, the acidic environment suppresses the interaction of the basic groups of the peptides or proteins with surface silanols in the column packing. In some embodiments, the mobile phases comprise about 0.05% TFA in HPLC grade water and about 0.04% TFA in HPLC-grade acetonitrile.

In some embodiments, the reverse-phase HPLC column is a C-18 column having an octadecylsilica packing and with an inner diameter of 4.6 mm, a length of 150 mm, a particle size of 3 μm, and a pore size of 120 Å. Alternatively, strong cation exchange chromatography can be used. Strong cation exchange allows for separation of the carboxy-terminal fragments are separated from the non-carboxy-terminal fragments.

Once the non-carboxy-terminal fragments are isolated, they can be identified using mass spectrometry (MS) or liquid chromatography-mass spectrometry (LC-MS). FIG. 3 depicts the peptide alanine, and the diethylamide group of alanine. In performing the analysis, peptide or polypeptide chains having a diethylamide group at an end thereof can be identified by a resulting mass shift of 56.1 Da from the molecular weight of the natural peptide, such as that shown in FIG. 3.

B. Detection and Quantification of Peptide or Polypeptide Chains Having a Diethylamide Group at an End Thereof using NMR Another embodiment of the invention includes a method of detecting and quantifying non-natural amino acids, including amino acids having C-terminal diethylamide groups at one end thereof, in polypeptide mixtures, such as glatiramer acetate, utilizing NMR. NMR is a phenomenon which occurs when the nuclei of certain atoms are immersed in a static magnetic field and exposed to a second oscillating magnetic field. Some nuclei experience this phenomenon, and others do not, depending on whether they possess a spin characteristic. NMR spectroscopy can be used to study chemical structure.

Furthermore, NMR can be used for many molecules possessing a spin characteristic. These include, but are not limited to, $^{1}H$, $^{2}H$, $^{23}Na$, $^{15}N$, $^{13}C$, and $^{18}O$. More than 200 isotopes have magnetic moments and can be studied using NMR. NMR can be done in the solution and solid states, and all types of NMR experimental can be applied to the presently disclosed methods, including broad band decoupling, off-resonance decoupling, nuclear Overhauser enhancement (NOE), and two dimensional NMR (2D-NMR). Representative examples of NMR methods are, but are not limited to: one pulse experiments; spin decoupling and difference spectroscopy; multiple pulse experiments including simples echoes, J-modulation, population transfer, selective polarization transfer, non selective polarization transfer-INEPT, inverse INEPT, Refocused INEPT; 2D-NMR including a basic two-dimension sequence, methods involving removing hetronuclear and/or homonuclear coupling; inverse-detected spectra-HMQC, homonuclear shift correlation experiments-COSY; variations on COSY, multiple quantum coherence-INADEQUATE, spin locked sequences-TOCSY, solvent suppressed two-dimensional spectroscopy, three dimensional NMR; methods studying connections through bonds; methods studying connections through space i.e., NOE experiments, including NOESY and ROESY; and methods measuring relaxation rates including inversion recovery, saturation recovery, and progressive saturation.

The presently disclosed NMR methods optionally can include methods for suppressing signals arising from solvents, buffers, and/or contaminants, including, but not limited to, presaturation or flip-back techniques.

In these embodiments, the polypeptide mixture can be analyzed in its intact or denatured form, with or without depolymerization. Depolymerization can be carried out using any of the methods described hereinabove.

The polypeptide mixtures to be analyzed can be in many forms, and commercially-available samples of polypeptide mixtures, such as glatiramer acetate, are typically available in lyophilized form. To initially prepare a sample including mixtures of polypeptides, pharmacological carrier agents, such as mannitol, can be removed using known methods, such as buffer exchange. Then, the sample can be redissolved in a solvent, such as $D_2O$. The sample can be dissolved in an appropriate buffer, such as Tris (tris-2,3-dibromo-1-propanol phosphate).

Different types of NMR methods can be performed on samples to determine properties of the peptides in the samples and to identify and quantify moieties therein. Multiple NMR methods, including multidimensional NMR methods, can be performed on small-quantity samples to both identify species and quantify their relative molar quantities. In addition to 1D proton NMR, two-dimensional heteronuclear single quantum correlation spectroscopy using 1H and 13C (2D HSQC) is useful for determining direct carbon/proton coupling and for integration, as explained below.

In some embodiments, 2D total correlation spectroscopy (TOCSY) can be used for determining proton/proton coupling and for integration. 2D correlation spectroscopy (COSY) can be used for determining proton/proton coupling and for integration. 2D nuclear Overhauser effect spectroscopy (NOESY) or rotational Overhauser effect spectroscopy (ROESY) can be used for determining through space proton/proton interaction. 3D NOESY-HSQC and 3D ROESY-HSQC also can be used to verify chemical shift assignments.

In some embodiments, a combination of NMR methods can be used to detect or identify the macromolecules in a mixture. For example, in the following example 1D $^1H$ NMR and 2D TOCSY NMR were used to identify and quantify diethylamide adducts.

Using the 1D 1H NMR spectrum, the area under each peak is measured relative to other identified peaks to determine the relative molar content of individual species. Therefore, using this analytical technique, the mol % of each species identified on the NMR spectrum can be calculated. The mol % of each species can be calculated by comparison of peaks from the same polypeptide species, while absolute amounts of each species may be determined through the use of a calibrated reference signal. A reference signal can come from another molecule in the sample or from a calibrated radiofrequency source.

Accordingly, by using either the enzymatic digestion followed by MS or LC-MS method as described herein or the multidimensional NMR as described herein, it is possible to measure and quantify the levels of diethylamide adducts in a polypeptide mixture.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Analysis of Diethylamide Adducts in Glatiramer Acetate

This example shows a way to detect and quantify DEA adducts in a copolymer preparation by NMR.

Signature NMR signals from diethylamide adducts were determined from Ala-Ala-diethylamide. The 1D $^1H$ NMR spectrum is shown in FIG. 5. The sample was dissolved in 700 µL 10-mM Tris-d11, pH 8 with 4-mM 2,2-dimethyl-2-silapentane-5-sulfonate-$d_6$ sodium salt (DSS-$d_6$). Chemical shifts were determined relative to the methyl $^1H$ of DSS. The two methyl groups of the diethylamide moiety produce distinct signals at 1.26 and 1.09 ppm.

Samples from a batch of glatiramer acetate (COPAXONE®) were analyzed by 1D $^1H$ NMR. Approximately 0.700 mL of formulated glatiramer acetate was lyophilized to dryness. The powder was redissolved in 0.700 mL $D_2O$ and lyophilized. The dissolution and lyophilization process was repeated three times. The sample was then redissolved in 0.700 mL 10-mM Tris-d11, pH 8 with 4-mM DSS-$d_6$. FIG. 6 is the 1D $^1H$ NMR spectrum for glatiramer acetate with suppression of the residual solvent signal. The large signals from 3.65-3.90 ppm arise from mannitol and the large signal at 1.92 ppm is from acetate used in formulating glatiramer acetate. The methyl $^1H$ signals of the diethylamide adducts are visible at 1.25 and 1.10 ppm. While they overlap the tail of the alanine methyl signals, the baseline is sufficiently smooth to subtract the broad feature and obtain a locally flat baseline for integration (FIG. 7). The signal from the feature at 3.00 ppm arises from the sum of lysine Hε and tyrosine Hβ. Each lysine and each tyrosine residue has two $^1H$ nuclei that give rise to this signal. Thus, the signal at 3.00 ppm is proportional to twice the content of lysine and tyrosine. The diethylamide methyl signal at 1.10 ppm is proportional to three times the diethylamide adduct content, as each methyl group has three $^1H$ nuclei.

The quantity of diethylamide can be determined from the ratio of the diethylamide methyl signal to the polypeptide signal at 3.00 ppm. From amino acid analysis, it was found that this batch of glatiramer acetate consists of 33.7% lysine and 9.1% tyrosine. Diethylamide therefore accounts for (2*[1.10 ppm integral]*([mol % Lys]+[mol % Tyr]))/(3*[3.00 ppm integral])=(2*1.00*42.8%)/(3*193.16)=0.14 mole % of residues. Alternatively, this value can be translated into total mass of diethylamide adduct or mol % of chains.

Similar values were obtained with multiple samples of glatiramer acetate from multiple batches, either with or without mannitol. The samples were stored as per the manufacturer's instructions before analysis.

Example 2

LC/MS Analysis of Diethylamine

This example shows a way to detect and quantify DEA adducts in a copolymer preparation by mass spectrometry.

Various modifications of terminal residues in the polypeptide chains of Copolymer-1 can occur from various reaction pathways. For example, modifications of the N- and C-terminal residues, such as DEA at the C-terminus, can occur. These modifications are a direct result of the production process of Copolymer-1. Monitoring these modifications can provide information about the process. If these species are present in a significant amount, they may need to be quantified as impurities.

Mass spectral evidence of the existence of DEA is shown in FIGS. 8A and 8B. DEA has also been detected by NMR.

Referring now to FIGS. 8A and 8B, FIG. 8A shows a representative DEA MS/MS fragmentation pattern. The amide bond between DEA and the carboxylic group of a peptide is fragile and can break by collision with gas molecules, such as nitrogen. In source fragmentation, compounds are fragmented into smaller fragments in an ion source, and can generate some types of fragment ions, such as DEA ions. An ion with the same mass as DEA, 74.09, was generated by in-source fragmentation of a Copolymer-1 sample. FIG. 8B shows that the MS/MS fragmentation of this ion generates the same pattern as DEA.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method comprising:
   (a) providing a sample of a composition comprising a copolymer of Glu, Ala, Lys, and Tyr;
   (b) determining, in the sample of the composition, the amount of polypeptides having a having a diethylamide-modified C-terminal amino acid, wherein the determining step comprises:
   fragmenting the copolymer, and
   measuring the level of diethylamide in the fragmented copolymer by detecting diethylamide; and
   (c) preparing a pharmaceutical composition comprising glatiramer acetate using at least a portion of the composition comprising the copolymer of Glu, Ala, Lys, and Tyr if the amount of polypeptides in the sample having a diethylamide-modified C-terminal amino acid is about 7 mol % to about 20 mol %.

2. The method of claim 1, wherein a pharmaceutical composition comprising glatiramer acetate is prepared using at least a portion of the composition comprising the copolymer if the amount of polypeptides in the sample having a diethylamide-modified C-terminal amino acid is about 8 mol % to about 18 mol %.

3. The method of claim 1, wherein a pharmaceutical composition comprising glatiramer acetate is prepared using at least a portion of the composition comprising the copolymer if the amount of polypeptides in the sample having a diethylamide-modified C-terminal amino acid is about 10 mol % to about 15 mol %.

4. The method of claim 1, wherein a pharmaceutical composition comprising glatiramer acetate is prepared using at least a portion of the composition comprising the copolymer if the amount of polypeptides in the sample having a diethylamide-modified C-terminal amino acid is about 12 mol % to about 14 mol %.

5. The method of claim 1, wherein the step of detecting diethylamide comprises the use of a technique selected from the group consisting of: mass spectrometry, liquid chromatography/mass spectrometry, and NMR spectroscopy.

6. The method of claim 1, wherein the step of providing the sample of the composition comprising the copolymer of Glu, Ala, Lys, and Tyr comprises: polymerizing a mixture of Glu (OBn)-N-carboxy anhydride, Ala-N-carboxy anhydride, Lys (trifluoroacetyl)-N-carboxy anhydride, and Tyr-N-carboxy anhydride to generate Intermediate-1, treating the Intermediate-1 with 33% HBr/Acetic Acid to generate Intermediate-2, and treating the Intermediate-2 with piperidine to generate Intermediate-3.

7. The method of claim 1, wherein detecting comprises use of tandem mass spectrometry.

* * * * *